United States Patent [19]

Lenczyk

[11] Patent Number: 4,590,317
[45] Date of Patent: May 20, 1986

[54] PROCESS FOR MINIMIZING CORROSION AND COKING IN AN ETHYLENE DICHLORIDE PLANT

[75] Inventor: John P. Lenczyk, Akron, Ohio

[73] Assignee: The B. F. Goodrich Company, Akron, Ohio

[21] Appl. No.: 637,982

[22] Filed: Aug. 6, 1984

[51] Int. Cl.$^4$ .............................................. C07C 17/00
[52] U.S. Cl. ................................... 570/220; 570/262; 570/241; 570/254; 570/226; 570/227
[58] Field of Search ............... 570/220, 262, 222, 241, 570/254, 255, 226, 227

[56] References Cited

U.S. PATENT DOCUMENTS

| | | | |
|---|---|---|---|
| 3,691,239 | 9/1972 | Hackett et al. | 570/262 |
| 3,839,475 | 10/1974 | Kurtz et al. | 570/262 |
| 4,029,714 | 6/1977 | Ziegenhagen et al. | 570/247 |
| 4,329,323 | 5/1982 | Shiozaki et al. | 570/254 |

FOREIGN PATENT DOCUMENTS

| | | | |
|---|---|---|---|
| 691354 | 7/1964 | Canada | 570/226 |
| 86387 | of 1971 | German Democratic Rep. | 570/254 |

Primary Examiner—Charles F. Warren
Assistant Examiner—Joseph A. Boska
Attorney, Agent, or Firm—Alfred D. Lobo; Alan A. Csontos

[57] ABSTRACT

A process is disclosed for the economical operation of a commercial ethylene dichloride (EDC) cracking furnace which typically is prone to coking of the tubes through which the EDC is flowed. The EDC cracking furnace is found to be critically sensitive to the presence of trace amounts, 30 ppm or more of FeCl$_3$ and/or 20 ppm or more of free chlorine, which cause coking of the tubes of the furnace. The coking of the tubes is minimized by maintaining less than 30 ppm by weight of FeCl$_3$ or less than 20 ppm of free chlorine in the EDC feed to the EDC furnace. In the particular instance where EDC is produced at least in part in a high temperature direct chlorination ("boiling") reactor constructed from mild steel, this goal requires that the chlorine content of the effluent from the boiling reactor be controlled so as not to exceed 20 ppm. But this is to be done without using more than a 2% by weight excess of ethylene over the stoichiometric amount required to produce the EDC in the boiling reactor. The goal is met by controlling the pressure drop and contact time through a polishing reactor, provided the operation of the boiling reactor is also controlled. The requirements are met with a packed bed of catalyst support having a geometry such that the outer surface area per unit volume of packed catalyst is less than 7.8 cm$^2$/ml and the catalyst support has a wall thickness of from about 2.5 mm to about 6.5 mm. The polishing reactor removes the FeCl$_3$ which may be present and also allows the conversion of at least 90% of the free chlorine in the chlorine-rich EDC (100 ppm to about 3000 ppm Cl$_2$). This results in continuous operation of the EDC furnace for much longer periods than is normal without the use of a polishing reactor.

9 Claims, 1 Drawing Figure

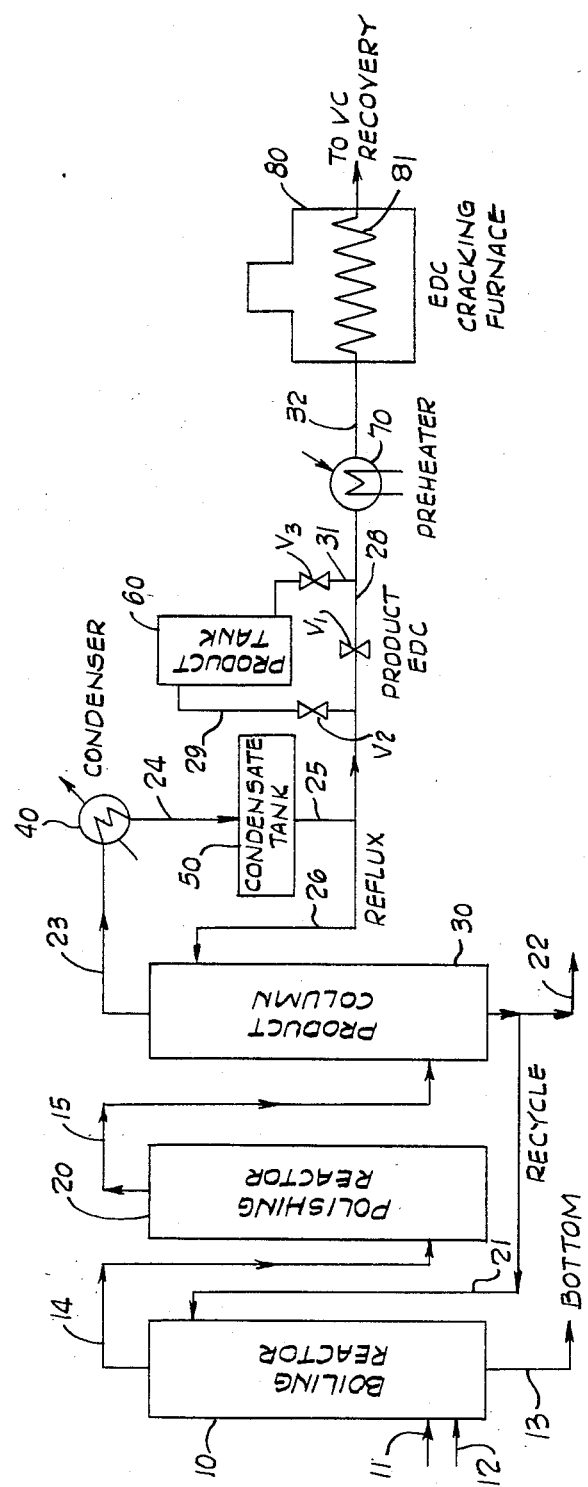

PROCESS FOR MINIMIZING CORROSION AND COKING IN AN ETHYLENE DICHLORIDE PLANT

BACKGROUND OF THE INVENTION

This invention is directed to the operation of an ethylene dichloride ("EDC") cracking furnace such as is used to produce vinyl chloride ("VC") monomer from EDC feed. During operation the equipment, if not made from a suitable alloy, is subject to corrosion, and particularly the furnace, though fitted with alloy tubes, is subject to coking. When this occurs, the furnace, and the preheater for feed to the furnace, must be shut down and cooled. The preheater is then manually, laboriously cleaned, and the furnace decoked.

Since the commercial production of vinyl chloride monomer ("VCM") is a continuous operation in which a typical furnace cannot economically produce less than about 100 million pounds per year (MM lb/yr) of VCM, it will be appreciated that shutting down the furnace for any reason, no matter how compelling, is not happily tolerated.

It has recently been found that only a trace, as little as 10 parts per million (ppm) by weight of iron present as ferric chloride ($FeCl_3$) will effectively force a 100 MM lbs/yr cracking furnace to be shut down after only about three weeks of operation. The $FeCl_3$ is typically generated in ferrous metal pipes through which EDC is fed to the furnace, or to a lesser extent, may be carried over from a catalytic reactor in which EDC is generated by the reaction of ethylene and chlorine in the presence of $FeCl_3$ catalyst.

The problem of maintaining less than the trace quantity of $FeCl_3$ in the EDC is exacerbated because (a) the liquid phase chlorination of ethylene requires a $FeCl_3$ catalyst, and (b) the reactor in which the EDC is produced is made of a ferrous metal, particularly carbon (mild) steel, for economic reasons. When a high nickel alloy such as Hastelloy, Inconel, or a titanium or glass-lined reactor is used, the only $FeCl_3$ to be contended with is the entrained catalyst, which is not difficult. If the effluent from the alloy or titanium reactor is led through non-ferrous or glass-lined piping to non-ferrous or glass-lined storage tanks, the problem of coking due to $FeCl_3$ in the tubes of the EDC furnace essentially disappears. But even in an all-alloy plant, if 20 ppm or more free chlorine is present in the feed to the EDC furnace, the tubes coke up.

When the stored EDC is preheated before it is fed to the EDC furnace, and such heating is done in a ferrous metal heat exchanger (preheater), the corrosion and coking problems are revived. If the feed to the furnace is preheated in an alloy preheater, and there is 20 ppm or more of free chlorine present, the coking problem is revived.

Stated differently, the problem of corrosion in piping, storage tanks, heat exchangers, etc., and coking of the tubes of an EDC cracking furnace can be effectively negated only by carefully guarding against the presence of either 30 ppm of $FeCl_3$, or 20 ppm free chlorine, or both, in the feed to the furnace. Because the cost of building an all alloy EDC plant is economically difficult to justify, as much of the equipment as possible is constructed with ferrous metals, particularly carbon steel. More specifically, since the cost of a boiling reactor used in the high temperature direct chlorination (HTDC) of ethylene militates in favor of a carbon steel one, the problems of corrosion in the equipment train, and coking of the EDC furnace are both problems to which an economical solution is sought.

Therefore this invention is most particularly directed to minimizing the corrosion in an EDC plant, and particularly the coking of the EDC cracking furnace in a plant where the EDC is generated in a boiling reactor reactor made from ferrous metal such as carbon steel; where, even if an alloy reactor is used, the EDC produced is stored in carbon steel storage tanks; or where, even if made in an alloy reactor and stored in an alloy storage tank, the liquid EDC feed to the furnace contains 20 ppm or more of free chlorine which EDC is vaporized in a carbon steel preheater; in any of which situations, the sensitivity of the equipment to corrosion due to free chlorine, and coking of the furnace due to the presence of trace quantities of either $FeCl_3$ or free chlorine, becomes of prime importance.

In view of the specificity of the problem stated hereinabove, this invention is of most value in an EDC plant where the boiling reactor provides the driving force for the feed to the EDC furnace. Such a reactor is operated at the boiling point of EDC, typically under pressure of up to about 50 $lb/in^2$ gauge (psig), under a wide range of other operating variables (i) to minimize the entrainment of $FeCl_3$ catalyst in the reactor; (ii) to minimize the production of unwanted byproducts; and, (iii) to maintain as low an excess of ethylene over stoichiometric as is practical to minimize the amount of unreacted (free) chlorine in the effluent from the reactor. Further, since excess ethylene cannot be economically recovered, any such ethylene is not only wasted but 'rides' through the system at considerable cost. The deceptively simply stated goal is to convert all the chlorine fed to the EDC reactor with a minimum excess of ethylene, and to avoid forming as little as 30 ppm of $FeCl_3$ (10 ppm as Fe, and about 20 ppm as Cl) in the feed to the EDC reactor.

As is well known, the economics of chemical engineering unit operations in the production of EDC from VC monomer are such that, optimally, the ethylene and chlorine are converted to EDC without the formation of unwanted byproducts and most important, without leaving any free chlorine residue in the effluent. The problem of corrosion is discussed in "Alloy Selection for VCM Plants" by Schillmoller, C. M., *Hydrocarbon Processing* pg 89–93, March 1979.

In practice, economics dictate that the direct chlorination reaction be controlled so that carbon steel equipment may be used. The problem is that as little as from about 20 ppm to about 60 ppm of free chlorine in carbon steel equipment and piping upstream of the EDC reactor has a highly corrosive effect on its tubes. The problem is further magnified when trace amounts of moisture in the range from 10 ppm to about 50 ppm are also present.

In the course of culling the numerous variables to select those which critically affect the viability of the commercial process, it was further discovered that the "make" of unwanted byproducts was a function of the temperature at which the boiling reactor operates, the higher the temperature the greater the make. This relationship dictated that the boiling reactor be operated at as low a pressure as was practicable.

To minimize the amount of unreacted chlorine leaving the reactor (referred to herein as "free" or "breakthrough" chlorine), an excess of ethylene is supplied to it. By "excess ethylene" we refer herein to ethylene in an amount greater than that stoichiometrically required to produce EDC. However, even when more than 2% excess ethylene is supplied, the amount of free chlorine in the effluent remains in the range from about 100 ppm to about 3000 ppm, and substantially all of it has to be removed. Thus, after having selected the critical variables it was necessary to tailor each one within narrow limits which would effectively provide the results sought, namely desirably coke-free operation of the EDC cracking furnace.

We do not know of any prior art reference which has recognized, much less addressed the problem a trace quantity (from 30 ppm to about 100 ppm) of $FeCl_3$ presents in an EDC furnace. We are well aware that the problem of minimizing corrosion due to the effluent, without specific regard as to minimizing the production of free chlorine and its effect on process equipment in an EDC plant, has confronted many persons skilled in the art. Corrosion is pronounced even at room temperature; it gets exponentially worse, doubling for every 10° C. increase, so that in the range above 50° C. it is in full effect; and, if one wishes to operate a commercial boiling reactor, one cannot avoid operating in the elevated temperature range.

To minimize corrosion in the equipment generally, in such a manner as to provide an effluent which is not only acceptably corrosive but economically not unduly burdensome is a difficult problem to which a better solution is constantly sought; but, to do so with specific regard to the trouble-free low coking operation of an EDC furnace adds to the difficulty of solving the problem. Part of the difficulty lies with the varied considerations which define the problem, as it presents itself in different guises, hence the elusiveness of the solution; and by no means a minor part lies in the unforgiving economics of any solution to the problem. It is axiomatic that solutions to industrial problems must be economically acceptable.

It is well known that $FeCl_3$ is an addition catalyst which catalyzes the chlorination of ethylene, of EDC, and of VC; and, the formation of ethyl chloride by the addition of HCl to VC. During operation of an oxychlorination reactor Shiozaki et al in U.S. Pat. No. 4,329,323 teach that $FeCl_3$ from the reactor "may transpire from the reactor or cause troubles such as choking of the reactor" (col 1, lines 51-52). They recognized that the catalyst itself might lead to an unacceptably high pressure drop. Their problem was to remove ethylene and VC simultaneously; and, to do so they inject chlorine which must be present in excess (up to 15 mol % excess). When they inject the chlorine they created the problem which we were to address. Shiozaki et al were unconcerned with the effectiveness of the EDC furnace, nor did they recognize that trace quantities of free chlorine would vitiate its effectiveness. Neither were they concerned with the formation of ethyl chloride and/or 1,1,2-trichloroethane ('triane'). To cope with the pressure drop they used catalyst having arbitrary geometry but an outer surface area per unit packed catalyst volume of not less than 7.8 $cm^2$/ml. This catalyst creates too high a pressure drop if used to remove chlorine from the effluent of a boiling reactor.

U.S. Pat. No. 4,029,714 to Ziegenhagen et al teaches a process analogous to that described by Shiozaki et al, in which a chlorine-removal system comprising a heat exchanger, a fixed bed reactor (referred to herein as a "polishing reactor") and a separator, is placed immediately down-stream of an ethylene clean-up system, and the combination is operated at a greater chlorine-to-ethylene feed ratio than the up-to-10% molar excess with respect to ethylene (typically used). Like Shiozaki et al, they stressed the effectiveness of a supported ferric chloride catalyst in combination with metallic iron, but concluded the effectiveness of the process was predicated upon a choice of the proper ratio of the superficial area of the iron to the total BET surface area of the alumina, without regard to catalyst geometry or contact time.

Like the Shiozaki et al process, the '714 process recognized the problem of a very long catalyst bed contributing to a high pressure drop and specifically selected a catalyst with sufficient activity to avoid the problem, not recognizing that extended contact times would favor formation of ethyl chloride, etc., or that generation of $FeCl_3$ in the bed by reaction of chlorine with the iron, itself could create enough of a pressure drop to choke the reactor. But pressure drop was not critical except if it approached a level threatening to choke the reactor. Extended contact time and relatively high pressure drop are unrelated to the operation of the oxychlorination reactor in which the EDC is generated because, unlike a boiling reactor, the operation of an oxychlorination reactor is far less sensitive to increased pressure.

Thus in each of the foregoing '323 and '714 processes, ethylene is fed to an ethylene clean-up reactor along with at least enough chlorine to react with it, the ethylene feed containing HCl and chlorinated hydrocarbons from an oxychlorination reactor. The '714 reference teaches that the cleaned-up chlorine-rich stream, with as much or as little chlorine as is left unreacted, is then led to the polishing reactor, where, given a long enough bed of an activated alumina catalyst impregnated with $FeCl_3$, low levels of ethylene and chlorine may be reached in the polished effluent. But the contact time would be so great as to convert valuable EDC and VC to triane and ethyl chloride respectively, inter alia, neither of which can be economically recovered, and the pressure drop would be so high as to preclude the operation of a boiling reactor operating at about 600 MM lb/yr rate of EDC production.

SUMMARY OF THE INVENTION

It has been discovered that the economical operation of a commercial EDC cracking furnace, is unexpectedly critically sensitive to the presence of trace amounts of free chlorine and/or $FeCl_3$ contaminants in EDC (contaminated EDC), either of which contaminants causes coking of the furnace; and that, contaminated EDC may be purified (or 'polished') in a polishing reactor.

It has also been discovered that the source of the coking problem in an EDC furnace is the presence of either 30 ppm or more of $FeCl_3$ by wt based on EDC, or 20 ppm by wt free chlorine, both of which can be controlled with a contact time of less than 10 sec in the polishing reactor.

In the particular case where the EDC is produced in a boiling reactor, it has been discovered that control of the contaminants can be exercised in the polishing reactor to which effluent from the boiling reactor is flowed, without feeding more than a 2% by weight excess of ethylene to the reactor, over the stoichiometric amount required to produce the EDC.

To meet the goal of maximized production of EDC in a boiling reactor with a minimum make of unwanted byproducts, and yet to meet the foregoing requirements by using a polishing reactor, it has been discovered that the pressure drop through the polishing reactor is the essential variable which must be critically controlled so that the boiling reactor may be operated in the range from 1 atmosphere (atm) to about 1.5 atm, outside which range the make of contaminants is too high to be effectively controlled by the polishing reactor.

Further, in a boiling reactor having a rated throughput of at least 500 MM lb/yr of EDC, the entire effluent from which boiling reactor is to be polished in one or more polishing reactors each containing an alumina or titania catalyst support optionally impregnated with $FeCl_3$ as the predominant active ingredient, it has been found that the polishing reactor is necessarily a fixed bed reactor in which the catalyst geometry is such that the outer surface area per unit volume of packed catalyst is less than 7.8 $cm^2$/ml and has a wall thickness of from about 2.5 mm to about 6.5 mm, which geometry is best satisfied by tubular catalyst sections.

It is therefore a general object of this invention to provide a process which minimizes the corrosion caused by free chlorine in an EDC plant, and coking caused by either free chlorine or $FeCl_3$ in an EDC cracking furnace, comprising, flowing contaminated EDC through a polishing reactor which contains a fixed bed of the aforesaid catalyst having the prescribed surface area per unit volume and suitable geometry, and operating the polishing reactor at a temperature in the range from 85° C. to 130° C. with a pressure drop less than 10 psi and a contact time less than 10 sec, so as to provide an essentially chlorine-free and $FeCl_3$-free feed to the EDC furnace, or, to a carbon steel preheater for this feed, if such a preheater is used.

BRIEF DESCRIPTION OF THE DRAWINGS

The foregoing and other objects and advantages of this invention will appear more fully from the following description, made in connection with the accompanying drawing schematically illustrating a preferred embodiment of the invention, in which drawing:

The FIGURE is a simplified schematic flow diagram illustrating the relationship of a typical boiling reactor, a polishing reactor, a product column, a cracking furnace, and related equipment used to process the flow of effluent from each processing step in a conventional vinyl chloride monomer ("VCM") plant.

DETAILED DESCRIPTION OF THE PREFERRED EMBODIMENT

In the preferred embodiment, minimizing coking improves the efficiency of an EDC pyrolysis ("cracking") furnace such as is used in the commercial production of VC monomer. In a large plant VC monomer is preferably produced in a "balanced" process, referring to the use of both oxchlorination and direct chlorination reactors to produce EDC for feed to the EDC furnace(s), as is described more fully in the chapter titled "Vinyl Polymers (Vinyl Chloride)" by Cowfer, J. A. and Magistro, A. J., *Encyclopedia of Chemical Technology, Kirk-Othmer,* Vol. 23, 3rd Ed. pp 865-885, John Wiley & Sons 1983, and the references cited therein, pertinent portions of which are incorporated by reference thereto as if fully set forth herein.

We have attributed the problem of premature coking of the EDC furnace to as little as 30 ppm of $FeCl_3$, without regard for the source of the $FeCl_3$. As has already been pointed out, keeping out $FeCl_3$ which may be entrained from the boiling reactor is relatively easy, but even if all the equipment in the EDC equipment train upstream of the EDC furnace was incapable of contributing Fe to react with free chlorine, the problem of coking up the EDC furnace would still arise if 20 ppm or more of free chlorine was present.

Since it is economically necessary to use ferrous metal at least in some portions of the plant, any such ferrous metal contributes Fe to free chlorine, and, particularly in the presence of trace amounts of moisture (5 to 50 ppm), the corrosion problem in process equipment upstream of the EDC furnace and the coking of the furnace, may shut down a commercial operation. Such conditions of free chlorine and moisture are not experienced in an oxychlorination reactor because its effluent contains essentially no free chlorine, but are peculiar to a boiling reactor. The effluent from an oxychlorination reactor also contains a substantial amount of HCl even when operation is controlled to get maximum conversion of HCl. A boiling reactor has relatively very little HCl in its effluent, and at least 50 times, generally from about 50 times to 100 times as much ethylene as there is free chlorine.

Though the reaction kinetics of the direct chlorination reaction dictate that the larger the excess ethylene fed to the boiling reactor the less the free chlorine in the effluent, such decrease in free chlorine as is obtained with more than 3% excess ethylene is not economically justified. For an EDC capacity of 600 MM lb/yr a boiling reactor requiring a 1% excess ethylene wastes 1.7 MM lb/yr of ethylene which is not recovered. Therefore it is of great importance that the amount of excess ethylene be controlled to a minimum, preferably in the range from about 0.05% to 2%, more preferably to 1%, and that the process conditions be controlled in the boiling reactor to get maximum ethylene efficiency. "Ethylene efficiency" is defined as the amount of ethylene converted to EDC divided by the total amount of ethylene fed.

To obtain acceptable ethylene efficiency it has been found that the temperature of the boiling reactor is required to be maintained in the range from about 83° C. to about 120° C., more preferably from 85°-100° C., so that the pressure is most preferably slightly above 1 atm, generally in the range from 1 atm to about 1.3 atm, the precise operating pressure being determined by the vapor pressure of the components of the liquid in the reactor.

However, at progressively lower temperatures and corresponding pressures, the likelihood of liquid formation in a polishing reactor to remove free chlorine increases. If such liquid forms in the polishing reactor, the catalyst is 'blinded' decreasing the effectiveness of the catalyst, thus increasing the necessary contact time to react free chlorine, increasing the pressure drop, and denigrating the effectiveness of the polishing reactor.

Referring to the drawing, there is shown a schematic flow diagram of a particular instance wherein a ferrous metal boiling reactor 10 containing liquid EDC and a catalytic amount of $FeCl_3$ in the range from 1% to 10% by wt, is held under elevated pressure from about 1 atm to about 1.5 atm, at boiling point. A slight molar excess of ethylene, about 1% over the stoichiometric amount of chloride required to from EDC, is fed to the reactor through an ethylene feed line 11, and stoichiometric chlorine is fed through a chlorine feed line 12, both near the bottom, so that they react exothermically within the hot liquid EDC. The heat of reaction boils off EDC and the reaction is controlled so that the reaction mass is maintained at a preselected desried temperature. All piping in the plant is mild steel, as is all the equipment connected by the piping.

The chlorine is deliberately "doctored" with oxygen present in the range from about 0.1% to about 1% by wt of the combined flow of ethylene chlorine and oxygen, to increase the selectivity of EDC and to inhibit the free radical reactions which produce triane and other polychlorinated compounds having more than two (2) Cl atoms in each molecule. Though such polychlorinated compounds are undesirable, they are nevertheless unavoidably formed as byproducts of the reaction, but being higher boiling than EDC, tend to concentrate in the reaction mass. Therefore, a bottoms stream 13 is withdrawn from the reactor. The oxygen is conveniently introduced by injecting air into either the ethylene or the chlorine feed lines, each of the gases being thoroughly dried over a bed of dessicant to remove moisture.

Though the reaction is carried out with an excess of ethylene, there is always present a deleterious amount of contaminant chlorine. Further, despite attempts to provide all the reactants in as dry a form as practical, there is always present a small amount of moisture in the range from about 20 ppm to about 0.05%. This combination of free chlorine and moisture on the ferrous metal surfaces of the equipment produces $FeCl_3$ which must be minimized.

The effluent leaves the reactor near the top through an effluent line indicated generally by reference numeral 14, and is led into a polishing reactor 20, preferably near its bottom, for upward flow though downflow may be used. The polishing reactor 20 is packed with cylindrical sections of gamma alumina catalyst support impregnated with about 5% $FeCl_3$. The outside diameter of each section is about 1.59 cm, the axial bore being about 0.95 cm. The dimensions of the packed bed of catalyst are adjusted to provide a contact time of less than 10 sec during which at least 90% of the free chlorine is reacted. To get this efficiency, namely a conversion of at least 90% in less than 10 sec contact time, the gaseous effluent through the bed must remain in the vapor phase and the outer surface per unit volume of the packed catalyst is less than 7.8 $cm^2/ml$. In the best mode, this is accomplished with a wall thickness of from 2.5 mm to about 6.25 mm for each catalyst section in a bed of appropriate dimensions.

The predominant reaction in the bed is the chlorination of ethylene, very little VC being chlorinated. This reaction of $Cl_2$ with $C_2H_4$ has the characteristics of a first order reaction. It has been found that when the reaction constant 'k' is less than 0.32, the conversion of free chlorine is economically unacceptable.

The effluent in line 14 consists essentially of EDC contaminated with from about 100 ppm to about 0.3% by wt of chlorine, and/or 30 ppm to 100 ppm $FeCl_3$, and from 100 ppm to about 0.5% of oxygen, with comparable amounts less than 1% by wt of polychlorinated compounds. The amount of ethylene may be somewhat larger, preferably in the range from about a 0.05% to about a 1% molar excess, though the amount of this excess is not narrowly critical except to the extent that it affects the economics of the process.

The polished effluent from the polishing reactor 20 leaves through line 15 and is fed to the product column 30, near its bottom. The product column is a distillation column fitted with trays or other conventional vapor-liquid equilibria staging means (not shown). A portion of the bottoms from the product column is recycled to the boiling reactor through a recycle line 21 by a recycle pump (not shown) the remainder being withdrawn through bottoms line 22.

The overhead of the product column leaves through overhead line 23, is cooled in a condenser 40, and commercially pure liquid EDC (99.5+%) flows through line 24 and collected in condensate tank 50. This product EDC is withdrawn through line 25, a portion being refluxed through line 26 to near the top of the product column, the remainder being pumped through line 29 to product tank 60 where it is stored for later use. Lines 28, 29 and 31 are valved with valves $V_1$, $V_2$ and $V_3$ so that the product tank may be bypassed and EDC flowed directly to preheater 70. The preheater 70 is a modified shell and tube heat exchanger used to vaporize the EDC before it is piped through line 32 to the EDC cracking furnace 80. The EDC cracking furnace is of conventional design and serves to pyrolyze the EDC in coils 81 at from 450° C.–550° C. and at 100–350 psig pressure. VC vapor produced in the furnace is flowed to a VC recovery unit which is conventional and is not shown.

Though only a single polishing reactor is schematically illustrated in the process flowsheet drawn herein, it will be evident to one skilled in the art that it may be desirable to have plural polishing reactors arranged in parallel, one with the other(s), to meet the pressure drop and contact time requirements specified herein. Plural polishing reactors may also be desirable for operating convenience, as for example, when spent catalyst and fouled catalyst support from a polishing reactor are to be replaced with fresh catalyst and catalyst support without shutting down the entire process.

The following illustrative examples exemplify the operation of a polishing reactor which is fed with an EDC effluent from a boiling reactor in which effluent the concentration of free chlorine varies.

TABLE

|  | 1 | 2 | 3 | 4 | 5 |
|---|---|---|---|---|---|
| Inlet, ppm of $Cl_2$ | 271 | 370 | 387 | 402 | 524 |
| Outlet, ppm of $Cl_2$ | 19 | 10 | 2 | 10 | 25 |
| Reactor feed, lb/hr | 302 | 286 | 278 | 165 | 165 |
| Vapor velocity, ft/sec | 1.59 | 1.45 | 1.45 | 0.84 | 0.84 |
| *k ($sec^{-1}$) | 0.53 | 0.61 | 0.97 | 0.39 | 0.32 |

*k = ln (chlorine in, ppm/chlorine out, ppm)/contact time, sec.

In each of the five examples in the foregoing Table, the temperature of the effluent entering the polishing reactor is about 105° C., which is the operating temperature of the boiling reactor, and the pressure is about 16 psig (1.09 atm). The pressure drop through the up-flow polishing reactor was less than 10 psi with a fixed bed of $\frac{5}{8}''$ O.D. and $\frac{3}{8}''$ I.D. alumina catalyst cylindrical sections containing 5% by wt $FeCl_3$. Comparable results are obtained with a titania catalyst support of the same geometry containing the same active catalyst. A packed bed of catalyst support containing a mixture of cuprous chloride and cupric chloride also give good results, generally better than those obtained with a catalyst support containing no active catalytic ingredient(s).

The polished effluent is processed as shown in the FIGURE and fed to the EDC cracking furnace which operated for three times as long a period as is normal without the polishing reactor, before coking of the furnace tubes was noticeable.

Comparably coking-free operation of the EDC furnace is obtained when chlorine-rich EDC (up to 3000 ppm Cl$_2$) containing about 100 ppm FeCl$_3$ from a storage tank is vaporized, flowed through a polishing reactor under the process conditions specified for the polishing reactor, and fed to the preheater 70 for further heating prior to being pyrolized in the furnace.

I claim:

1. A process for reducing coking of an ethylene dichloride cracking furnace, corrosion of steel process equipment upstream of said furnace through which said ethylene dichloride is flowed, and other deleterious side effects due to the presence of trace amounts of ferric chloride and/or free chlorine in a gaseous feed to said furnace from a ferrous metal boiling reactor in which ethylene is directly chlorinated in the presence of a ferric chloride catalyst in boiling ethylene dichloride, said process comprising, (a) operating said boiling reactor with from 0.05% to 2% excess ethylene over the stoichiometric amount required to produce ethylene dichloride, (b) introducing the product consisting essentially of ethylene dichloride, contaminant amounts of oxygen, polychlorinated compounds each present in an amount less than about 0.5% by wt based on the weight of effluent flowed to the reactor, from 100 ppm to less than 524 ppm of free chlorine, and from 5 to 50 times as much ethylene as there is free chlorine, into a polishing reactor at a temperature in the range of from about 85° C. to about 130° C. and an inlet pressure in the range from greater than 1 atm to about 1.4 atm, (c) contacting said feed in said polishing reactor with a fixed bed of catalyst consisting essentially of tubular sections of a catalyst support selected from gamma alumina and titania optionally containing from about 5% to about 20% by wt of copper chloride or ferric chloride, said tubular sections having an outer surface area per unit volume of packed catalyst, of less than 7.8 cm$^2$/ml, and a wall thickness in the range from 2.5 mm to 6.5 mm, (d) maintaining a pressure drop of less than 10 psi through said polishing reactor, (e) evolving from said polishing reactor an essentially chlorine-free effluent having less than 10 ppm Fe present as FeCl$_3$, less than 20 ppm free chlorine and at least about 500 ppm ethylene, and, (f) introducing said essentially chlorine-free effluent into a cracking furnace to produce vinyl chloride.

2. The process of claim 1 wherein said free chlorine is present in the range from about 100 ppm to less than 524 ppm; said ethylene is present in the range from about 500 ppm to about 1%; said polychlorinated compounds are present in the range from about 50 ppm to about 1000 ppm; and said oxygen is present in the range from about 0.1% to about 1% by weight based on the weight of the ethylene dichloride flowed to said furnace.

3. The process of claim 2 wherein said catalyst support is impregnated with from about 5% to about 20% by wt of ferric chloride, and is in the form of cylindrical sections having a wall thickness of about 3 mm.

4. The process of claim 2 wherein step (a) includes operating said polishing reactor at a temperature in the range from 85° C. to about 120° C.

5. The process of claim 4 wherein step (a) includes introducing said contaminated ethylene dichloride into said polishing reactor, near the bottom thereof, and flowing said ethylene dichloride upward through said fixed bed of catalyst.

6. The process of claim 1 wherein said free chlorine is present in the range from about 100 ppm to less than 524 ppm; said ethylene is present in the range from about 500 ppm to about 1%; said polychlorinated compounds are present in the range from about 50 ppm to about 1000 ppm; and said oxygen is present in the range from about 0.1% to about 1% by weight based on the weight of the ethylene dichloride flowed to said furnace.

7. The process of claim 6 wherein said catalyst support is impregnated with from about 5% to about 20% by wt of ferric chloride, and is in the form of cylindrical sections having a wall thickness of about 3 mm.

8. The process of claim 6 wherein step (a) comprises operating said boiling reactor at a temperature in the range from 83° C. to about 120° C.

9. The process of claim 8 wherein step (b) comprises introducing effluent from said boiling reactor into said polishing reactor, near the bottom thereof, and flowing said effluent upward through said fixed bed of catalyst.

* * * * *